United States Patent [19]

Kado et al.

[11] Patent Number: 4,588,689
[45] Date of Patent: May 13, 1986

[54] RESTRICTION ENDONUCLEASE XCYI

[75] Inventors: Clarence I. Kado; Raymond L. Rodriguez, both of Davis; Byron E. Froman, West Sacramento; Robert C. Tait, Davis, all of Calif.

[73] Assignee: The Regents of the University of California, Berkeley, Calif.

[21] Appl. No.: 585,752

[22] Filed: Mar. 2, 1984

[51] Int. Cl.$^4$ .................. C12N 9/22; C12N 15/00; C12R 1/64
[52] U.S. Cl. .................. 435/199; 435/172.3; 435/910; 935/14
[58] Field of Search .................. 435/199, 172.3, 910

[56] References Cited

PUBLICATIONS

Endow and Roberts (1977) J. Mol. Biol. 112:521–529.
Kunkel et al. (1979) J. Mol. Biol. 132:133–139.

*Primary Examiner*—Lionel M. Shapiro
*Attorney, Agent, or Firm*—Bertram I. Rowland

[57] ABSTRACT

A novel restriction endonuclease designated XcyI recognizes and cleaves the sequence 5'-C ↓ CCGGG-3', where the arrow indicates the cleavage site. The enzyme may be obtained from *Xanthamonas cyanopsidis*.

*Xanthamonas cyanopsidis* strain 13D5 was deposited at the American Type Culture Collection on Jan. 20, 1984, and granted accession No. 39587.

4 Claims, No Drawings

RESTRICTION ENDONUCLEASE XCYI

BACKGROUND OF THE INVENTION

1. Field of the Invention

The ability to specifically cleave a duplex DNA molecule into discrete fragments is essential for the manipulation and modification of DNA in vitro. Such specific cleavage is accomplished using restriction endonucleases which are enzymes capable of cutting a DNA molecule at or about a specific recognition site. Type II restriction endonucleases recognize and cleave DNA at particular sequences of from four to seven nucleotides which usually have an axis of rotational symmetry. The site of cleavage may be within the recognition sequence or may lie a fixed number of base pairs away from the sequence. Moreover, the cleavage may be cut straight across the duplex producing flush or blunt-ended fragments, or may be staggered to produce either 5'- or 3'-cohesive ends.

Isoschizomers are different restriction enzymes which recognize the same target sequence and which may share a common cleavage pattern. Often, however, the isoschizomers will be affected differently by methylation of the substrate DNA. For example, while one member of an isoschizomer pair may be inhibited by methylation of a particular cytosine residue in the recognition sequence, the other member of the pair may be unaffected. Thus, two isoschizomers may produce different restriction patterns, depending on methylation of the DNA being cleaved.

To perform genetic manipulation in vitro, it is desirable to have a very large number of restriction endonucleases available to perform cleavage at preselected locations. Under certain circumstances, the use of one isoschizomer may be favored over another because of different cleavage patterns brought about by methylation of the substrate DNA. Moreover, one isoschizomer may be preferred over another because of greater inherent stability, greater purity from other contaminating enzymes, and the like.

2. Description of the Prior Art

Many restriction enzymes are reported in the literature, and a number of the reported enzymes are commercially available. Restriction enzyme XmaI recognizes the sequence 5'-CCCGGG-3' and cleaves between the first and second residues to produce a 5'-CCGG cohesive end. The isolation and use of XmaI are described by Endow and Roberts (1977) J. Mol. Biol. 112:521–529 and Kunkel et al. (1979) J. Mol. Biol. 132:133–139. The purification of XmaI is complicated by the presence of two other restriction enzymes, XmaII and XmaIII, and preparations of XmaI are often contaminated by these other enzyme activities. Moreover, XmaI is insufficiently stable to allow long-term storage and routine use.

SUMMARY OF THE INVENTION

A novel restriction enzyme obtained from the bacterial strain *Xanthamonas cyanopsidis* is provided. The endonuclease, designated XcyI, cleaves the sequence 5'-C ↓ CCGGG-3', where the arrow indicates the cleavage site. XcyI can be isolated at a high degree of purity, being substantially free from contaminating exonuclease and endonuclease activities. The XcyI enzyme preparations appear to be stable and may be stored for long periods prior to use. XcyI is an isoschizomer of both XmaI and SmaI and shares a common cleavage pattern with XmaI.

DESCRIPTION OF THE SPECIFIC EMBODIMENTS

Restriction endonuclease XcyI is a Type II restriction enzyme which is an isoschizomer of both XmaI and SmaI. XcyI is isolated from bacterial strain *Xanthamonas cyanopsidis* and has been named in accordance with the nomenclature of Smith and Nathans (1973) J. Mol. Biol. 81:419–423. Optimal enzyme activity is obtained at about 37° C.

XcyI may be isolated from *Xanthamonas cyanopsidis* strain 13D5, deposited with the American Type Culture Collection for patent purposes on Jan. 20, 1984, and granted accession No. 39587. Isolation may be performed using the rapid purification procedure of Greene et al. (1978) Nucl. Acids Res. 5:2373–2380. Cells are grown in a suitable culture medium, e.g., Luria broth, and suspended in an extraction buffer. The cell walls are lysed using lysozyme followed by sonication, the resulting lysate cleared of cell debris by centrifugation, and the supernatant decanted. The enzyme may be isolated from the supernatant by phosphocellulose chromatography followed by hydroxylapatite chromatography. Peak fractions are pooled and dialyzed, and the concentrated enzyme may be stored at −20° C. The enzyme preparation obtained by this procedure is substantially free from contaminating exonuclease and endonuclease activity.

Alternatively, XcyI may be produced by first isolating the gene which encodes XcyI and introducing the gene into an appropriate expression host. Methods for manipulating and identifying genetic material in vitro are now well known and need not be described in detail. Briefly, however, the XcyI gene may be isolated by first cleaving the chromosomal DNA, typically by endonuclease digestion or mechanical shearing, followed by cloning in an appropriate usually bacterial cloning vector. Clones carrying the XcyI gene may be selected and expanded. The XcyI gene may then be introduced into an expression host, either directly or by means of an expression vector. The XcyI gene product may then be isolated from the expression host by conventional means. The gene product will have an amino acid sequence which is substantially identical to the naturally-occurring product, usually differing by fewer than 5% of the amino acids.

Substrate DNA may be restricted in a suitable buffer, e.g., Tris-HCl at pH 7.5, at 37° C. for a suitable time, e.g., 1 hour.

The following examples are offered by way of illustration, and not by way of limitation.

EXPERIMENTAL

MATERIALS AND METHODS

1. Growth of Cells

*Xanthamonas cyanopsidis* 13D5 was grown in Luria broth (LB) medium (Miller (1972) Experiments in Molecular Genetics, Cold Spring Harbor Laboratory, Cold Spring Harbor, N.Y.) at 30° C. in a rotary shaking incubator. A one liter culture grown for 20 hours yielded 5 gm of cells (wet weight).

2. Preparation of Cell Extract

The purification procedure of Greene et al. (1978) Nucl. Acids Res. 5:2373–2380 was followed with minor modifications. All steps were performed at 4° C. Extraction buffer (EB) was 10 mM $K_2HPO_4$-$KH_2PO_4$, pH 7.0, 7 mM 2-mercaptoethanol, 1 mM EDTA, 25 μg/ml phenylmethylsulfonyl fluoride, 1 mM $NaN_3$. Frozen cells (10 gm) were resuspended in 100 ml of EB +0.4 M NaCl. Lysozyme (10 mg) was added to the solution and dissolved by stirring. After 30 minutes, cells were lysed by sonication with a Heat System model W140D sonifier with a ½ inch probe. Sonication was performed at maximum power in three 60 second pulses. The lysate was cleared of cell debris by centrifugation in the Beckman Type 35 rotor (35,000 rpm, 4° C., 1 hour). The supernatant was decanted, diluted with EB to a conductivity equal to that of 0.2 M NaCl, and applied to a phosphocellulose column.

3. Phosphocellulose Chromatography

The crude extract was loaded onto a 2 cm×8.5 cm P-11 phosphocellulose column equilibrated in EB +0.2 M NaCl. The column was washed with EB +0.2 M NaCl until the $A_{280}$ was less then 0.05. A 300 ml gradient of 0.2 M NaCl–1 M NaCl in EB was applied to the column and 5 ml fractions were collected and assayed. XcyI activity eluted between fractions 12 and 30.

4. Hydroxylapatite Chromatography

Peak fractions from the phosphocellulose column were pooled and applied to a 1.5 cm×6 cm hydroxylapatite column equilibrated in EB. Activity was eluted with a 180 ml gradient of 0.01 M–0.50 potassium phosphate, pH 7.0, containing 1 mM EDTA, 7 mM 2-mercaptoethanol, 1 mM $NaN_3$, and 0.2 M NaCl. Fractions of 3 ml were collected and assayed for activity. XcyI eluted between fractions 12 and 30. Peak fractions were pooled and dialysed against storage buffer (50% glycerol, 20 mM potassium phosphate, pH 7.0, 0.2 M NaCl, 1 mM EDTA, 7 mM 2-mercaptoethanol, 1 mM $NaN_3$). The concentrated enzyme may be stored at −20° C.

5. XcyI Assay Conditions

Restriction reactions were performed in 6 mM Tris-HCl, pH 7.5, 6 mM 2-mercaptoethanol, 6 mM $MgCl_2$. Reactions of 18 μl volume containing 0.2 μg DNA were initiated by the addition of 2 μl of the fractions to be assayed. Reactions were incubated at 37° C. for 1 hour, then examined by agarose gel electrophoresis. Gels were run using the Tris-borate EDTA system (Bolivar et al. (1977) Gene 2:75–93) with 1% agarose submarine minigels.

6. Ligation Conditions

T4 DNA ligase was purified and used according to Tait et al. (1980) J. Mol Biol. 255:813–815.

7. DNA Sequencing

DNA sequencing was carried out according to the method of Sanger et al. (1977) Proc. Natl. Acad. Sci. USA 74:5463–5467. Plasmid DNA was denatured and primed for sequencing reactions as follows. Plasmid DNA (2 μg) was added to 18 μl dd$H_2O$ (twice distilled water). Following the addition of 2 μl of 2 N NaOH, 2 mM EDTA, and 5 minutes incubation at room temperature, the DNA was precipitated by the addition of 45 μl of 95% EtOH. The precipitate was collected by centrifugation in an Eppendorf microcentrifuge for 15 minutes at 4° C. The supernatant was poured off and the pellet dried 15 minutes in a vacuum over. The DNA pellet was resuspended in 3 μl of 2 M ammonium acetate, pH 4.8 + 10 μl dd$H_2O$ + 3 μl 3 M sodium acetate, pH 4.8. DNA was precipitated by the addition of 80 μl of 95% EtOH, incubated 10 minutes at 70° C., then centrifuged 15 minutes at 4° C. in a microcentrifuge. The supernatant was removed and the pellet washed once in 1 ml of cold 70% EtOH. The pellet was dried 15 minutes in a vacuum oven, resuspended in 15 μl dd$H_2O$, then used in the standard dideoxy-sequencing reactions. The "run-off" DNA synthesis reaction was essentially the same as the dideoxy A sequencing reaction except that XcyI cleaved denatured linear DNA was used as the template and the dideoxy ATP was omitted.

RESULTS AND DISCUSSION

Xanthamonas strains were initially screened on agarose minigels using phage lambda DNA as a substrate. On the basis of those results, the activity present in *X. cyanopsidis* 13D5 appeared to be an isoschizomer of SmaI. SmaI recognizes the sequence 5'-CCC ↓ GGG, and cleaves where indicated by the arrow. However, the DNA fragments generated by digestion of lambda DNA with SmaI are difficult to resolve on agarose minigels. A recombinant pSa727 plasmid containing a 25 kb KpnI-generated fragment of the *Agrobacterium tumefaciens* plasmid pTiC58 (Tait et al. (1983) Biotechnology 1:269–275) was also used as a substrate for screening. To verify that the digestion specificity of XcyI was the same as that of SmaI, this recombinant plasmid (pSa727:Kpn3) was digested with KpnI to generate a 15 kb vector DNA fragment that contains no SmaI cleavage sites and a 25 kb DNA fragment that contains 4 SmaI cleavage sites. Digestion of pSa727:Kpn3 with KpnI and SmaI or XcyI produced an identical restriction pattern, confirming that SmaI and XcyI are isoschizomers.

XcyI digested DNA was ligated with T4 DNA ligase at room temperature for 10 minutes, then examined by agarose gel electrophoresis. Ligation was efficient, and digestion of the ligation reaction with XcyI regenerated the original DNA fragments. Prolonged digestion of DNA with XcyI (72 hours) did not result in the appearance of additional DNA fragments or in the apparent loss or smearing of existing DNA bands. It has been previously demonstrated that the ability of T4 DNA ligase to ligate blunt ends can be inhibited by the presence of high concentrations of ATP (Ferretti and Sgaramella (1981) Nuc. Acids Res. 9:3695–3705). No difference was detected when XcyI digested DNA was ligated in the presence of 0.6 or 6.0 mM ATP, suggesting that the termini produced by XcyI are cohesive in nature.

In order to verify the cohesive nature of the termini and determine whether a 5' or 3' terminal extension was generated, the plasmid pUC8 (Vieira and Messing (1982) Gene 19:269–276) was digested with XcyI, then denatured. A 17 base pair primer and DNA polymerase I Klenow fragment were used to prime "run-off" DNA synthesis on the denatured linear plasmid DNA. The Klenow fragment will only elongate the primer to the point where the template DNA has been cleaved by the XcyI enzyme. When the products of this reaction are electrophoresed adjacent to a standard dideoxy-sequence of pUC8, the migration position of the run-off DNA synthesis reaction will correspond to the site cleaved by XcyI. The results indicated that XcyI cleaves the SmaI site of pUC8 between the first and second residues to generate a protruding 5'-CCGG. These results demonstrate that XcyI and XmaI recognize the same sequence and display an identical cleavage pattern.

It was observed that certain recognition sites are somewhat resistant to cleavage by XcyI. By increasing the amount of enzyme in the reaction, however, even recalcitrant sequences could be digested. It is possible that although XcyI recognizes and cleaves the sequence 5'-CCCGGG-3', the methylation of residues within or adjacent to this sequence may affect the function of the enzyme. Although purification of DNA from the dcm− strain *E. coli* GM48 increased the relative rate of cleavage of these sequences, the deficiency of cytosine methylation did not completely alleviate the inhibition of cleavage. The XcyI cleavage site in pUC88 is a slowly digested site, and it is located adjacent to a BamHI site. BamHI cleavage sites are believed to contain a recognition site for adenine methylase (Vander Ploeg and Flavell (1980) Cell 19:947–958).

According to the subject invention, a novel restriction endonuclease is provided which is capable of cleaving the sequence 5'-C↓CCGGG-3'. The enzyme is found to be particularly stable and may be isolated from *X. cyanopsidis* substantially free from contaminating enzymes.

Although the foregoing invention has been described in some detail by way of illustration and example for purposes of clarity of understanding, it will be understood that certain changes and modifications may be practiced within the scope of the appended claims.

What is claimed is:

1. A restriction endonuclease having substantially the same amino acid sequence as XcyI derived from *Xanthamonas cyanopsidis* 13D5, which endonuclease recognizes the sequence:

5'-C↓CCGGG-3', and cleaved where indicated by the arrow.

2. A restriction endonuclease as in claim 1, obtained by isolation of endonuclease from a culture of *Xanthamonas cyanopsidis* 13D5.

3. A method for preparing a restriction endonuclease which cleaves the sequence 5'-C↓CCGGG-3', where indicated by the arrow and is designated XcyI, said method comprising:

lysing cells of *Xanthamonas cyanopsidis* 13D5; freeing the resulting lysate of cell debris; and isolating XcyI from the supernatant.

4. The enzyme XcyI prepared in accordance with the method of claim 3.

* * * * *